United States Patent [19]

Yamasaki et al.

[11] Patent Number: 4,921,791

[45] Date of Patent: May 1, 1990

[54] METHOD FOR MEASURING SPECIFIC COMPONENT USING PEROXIDASE ENZYME REACTION

[75] Inventors: Masahiko Yamasaki; Satoshi Kawakatsu, both of Tokyo, Japan

[73] Assignee: Konishiroku Photo Industry Co., Ltd., Tokyo, Japan

[21] Appl. No.: 66,186

[22] Filed: Jun. 25, 1987

[30] Foreign Application Priority Data

Jun. 26, 1986 [JP] Japan ................................ 61-150723
Sep. 12, 1986 [JP] Japan ................................ 61-216299

[51] Int. Cl.$^5$ ..................... C12Q 1/00; C12Q 1/28; G01N 53/00; C12N 11/00
[52] U.S. Cl. .......................................... 435/28; 435/4; 435/7; 435/174
[58] Field of Search ...................... 435/28, 4, 174, 7

[56] References Cited

U.S. PATENT DOCUMENTS

| | | | |
|---|---|---|---|
| 4,567,136 | 1/1986 | Okaniwa et al. | 435/28 |
| 4,567,139 | 1/1986 | Batz | 435/28 |
| 4,596,768 | 6/1986 | Singh et al. | 435/28 |
| 4,665,023 | 5/1987 | Deneke et al. | 435/28 |
| 4,672,029 | 6/1987 | Washburn et al. | 435/28 |
| 4,716,110 | 12/1987 | Wada et al. | 435/28 |
| 4,729,950 | 3/1988 | Kricka et al. | 435/28 |
| 4,737,458 | 4/1988 | Batz et al. | 435/28 |
| 4,778,757 | 10/1988 | Teshima et al. | 435/28 |

FOREIGN PATENT DOCUMENTS

| | | | |
|---|---|---|---|
| 243126 | 4/1986 | European Pat. Off. | 435/28 |
| 252747 | 1/1988 | European Pat. Off. | |
| 56-055199 | 5/1981 | Japan | 435/28 |
| 60-218069 | 10/1985 | Japan | 435/28 |

OTHER PUBLICATIONS

Hawkes et al, Anal. Biochem., 119(1), 142–147, 1982.
Morrison et al., Organic Chemistry, 1963, p. 707, Allyn and Bacon Inc., Boston.

*Primary Examiner*—Robert J. Warden
*Assistant Examiner*—Laurie A. Scheiner
*Attorney, Agent, or Firm*—Finnegan, Henderson, Farabow, Garrett and Dunner

[57] ABSTRACT

A method for measuring a specific component, which comprises having a complex conjugate comprising a specific component to be measured and a labelled body having peroxidase as the label carried on a support, and forming and depositing a dye on said complex conjugate through the enzyme reaction of peroxidase by use of the three of hydrogen peroxide, an aromatic primary amine compound and either one of an active methylene compound or a phenol compound.

6 Claims, No Drawings

METHOD FOR MEASURING SPECIFIC COMPONENT USING PEROXIDASE ENZYME REACTION

FIELD OF THE INVENTION

This invention relates to a method for measuring a specific component, particularly a method for measuring a specific component to be carried out by use of an enzyme reaction of peroxidase.

DESCRIPTION OF THE PRIOR ART

Various analytical methods for detecting a specific component such as biological component have been developed, and among those methods, as the method with the highest precision, there has been known the method in which a specific binding reaction between said specific component and a substance capable of binding specifically thereto (hereinafter called specific binding substance), such as antigen and antibody, a certain kind of sugar chain and lectin, biotin and avidin, protein A and IgG, hormone and receptor, enzyme and substrate, etc.

Generally, by use of a specific binding substance attached with some label (hereinafter called labelled body), the specific component is measured by detecting the signal of said label which is changed depending on the specific component to be measured.

Particularly, there may be conveniently employed the method, in which a specific component carried directly or indirectly on a support is reacted with the labelled body to fix the labelled body as the conjugate of the both, and the signal is detected from the label corresponding substantially to the specific component.

For example, there may be included the method in which a proteinaceous biological component (specific component) electrophoresed is carried on a nitrocellulose film by transferring it from a gel and this is reacted with a labelled body such as an antibody labelled body for detection of the signal, the method in which a specific component such as a lipid, etc. developed on a TLC plate is reacted with a labelled body for detection of the signal, the method in which a DNA is reacted with a labelled complementary DNA to said DNA on a film for detection of the signal or the immunological histochemical staining method.

According to these methods, enormous information concerning not only quantitation of specific components and reactivities between specific components and specific binding substances, but also properties, existing states of the specific components or specific binding substances can be obtained. For example, in the method in which a signal is detected on a conjugate having a biological specific component such as a protein or a nucleic acid transferred and carried on a film after electrophoresis, or a lipid component developed on TLC bound to a labelled body for said specific component, information concerning the molecular weight, the isoelectric point or the polarity of said specific component can be obtained from the position, the mobility of the signal of the specific component.

Also, in the immunological histochemical staining method, information concerning the desired existing place, state, etc. in histology can be obtained.

In the measurement of a specific component as described above where a signal is detected corresponding substantially to the amount of the specific component on a complex conjugate carried directly or indirectly on a support, since the specific component to be measured is minute in amount, the label is required to be detected with high sensitivity, and also it is essentially required that the detection method of the label should have a high resolving power in order to obtain more information about the specific component.

For satisfying such requirements, as the label for the specific binding substance, there have been employed in the prior art radioisotopes, fluorescent substances, luminescent substances, enzymes, etc.

However, among them, when a radioisotope is used, there is the problem that enormous cost is required for attenuation, disposal, exposure of radioactivity or installation cost, and further during detection of the signal on the labelled body carried on a support, long time and cumbersome operations are disadvantageously required for exposure, development of light-sensitive photographic materials.

Also, when a fluorescent substance or a luminescent substance is used, a special device or equipment is required. On the other hand, when an enzyme is used, the operation is relatively simple and the dye formed can be readily visualized, and also quantitation of a specific component is possible. In the prior art, as such labelling enzyme, peroxidase, alkali phosphatase, $\beta$-galactosidase, etc. have been used. Particularly, in the method of forming and depositing a dye through the enzyme reaction on a complex conjugate carried on a support, peroxidase has been primarily used as the labelling enzyme, and during the reaction, as the substrate, diaminobenzidine, o-dianizidine, 4-chloro-1-naphthol, etc. have been used.

However, diaminobenzidine or o-dianizidine has the drawbacks such that it is strongly toxic and that background will readily appear. Although 4-chloro-1-naphthol is slightly higher in sensitivity as compared with other substrates, the sensitivity obtained cannot be said to be sufficient in order to measure a more minute amount of a specific component, or in order to obtain clearly more information about a specific component.

SUMMARY OF THE INVENTION

A first object of the present invention is to provide a method for measuring a specific component without use of a special device or equipment.

A second object of the present invention is to provide a method for measuring a specific component rapidly by a simple operation.

A third object of the present invention is to provide a method for measuring a specific component which can detect the label at high sensitivity even when the specific component may be minute in amount and yet can detect the label with high resolving power. The measurement method of the present invention is a method for measuring a specific component, which comprises having a complex conjugate comprising a specific component to be measured and a labelled body having peroxidase as the label carried on a support, and forming and depositing a dye on said complex conjugate through the enzyme reaction of peroxidase, characterized in that the three of hydrogen peroxide, an aromatic primary amine compound and either one of an active methylene compound or a phenol compound are used.

In the present invention, the specific component may be directly carried on the support through physical adsorption, chemical bonding such as ion bonding or covalent bonding, may be indirectly carried through one or more specific binding substances, and also carried comprehensively within the support. Also, the specific component may be carried directly or indirectly on the support before the reaction with said labelled body to form said complex conjugate, or alternatively said complex conjugate may be formed before said complex conjugate is carried directly or indirectly on the support. Further, the labelled body may be carried on the support under the state forming the complex conjugate with said specific component, and in this case, the specific component and the labelled body may be directly bonded to each other, or bonded through one or more other specific binding substances. Here, carrying on support means fixing on the surface or internally of support so as to be not releasable from the support.

Also, in the present invention, the labelled body may be labelled with a specific binding substance over-lappingly for peroxidase and anti-peroxidase antibody.

For the enzyme reaction of peroxidase in the complex conjugate, the three of hydrogen peroxide, an aromatic primary amine compound and an active methylene compound or a phenol compound are used. Through the action of peroxidase and hydrogen peroxide, the aromatic primary amine compound is oxidized, and then coupled with an active methylene compound or a phenol compound to form and deposit a dye.

As compared with the method of prior art described in Analytical Biochemistry 119, 142–147 (1982) by use of hydrogen peroxide and 4-chloro-1-naphthol as the substrate, the method of the present invention is shortened in color forming time, and the spot is clear and sensitivity is elevated by 10-fold or more. Also, as the result, the amount of the peroxidase labelled body can be reduced, which is also advantageous in cost.

In the present invention, the specific component to be measured is a substance or a group of substances capable of giving a specific binding substance which is bound specifically with the specific component.

For example, there may be included proteins, nucleic acids, hormones, lipids, complex glucides, glycolipids, polysaccharides, enzymes, vitamins, antigens, antibodies, etc.

The specific binding substance which can be used in the present invention is a substance capable of specifically binding with the specific component or another specific binding substance, and can be selected appropriately depending on the specific component to be measured. For example, there may be included proteins, nucleic acids, hormones, lipids, complex glucides, glycolipids, polysaccharides, enzymes, vitamins, antigens, antibodies, lectin, protein A, avidin, biotin, receptors, co-enzymes, substrates for enzymes, toxins, complements, and conjugates of these.

As the support which can be used in the present invention, there may be included films of cellulose acetate, nitrocellulose, etc.; gel-like support of polyacrylamide, etc., silica gel carrier of TLC plate, etc.; polysaccharides such as dextran, agarose, etc. and derivatives thereof; plate-shaped, bead-shaped plastics, glasses, metals, fibers, activated charcoal, hydroxyapatite, etc. Also, in histochemical staining, tissue itself can be also used as the support.

The aromatic primary amine compound available in the present invention may include o- or p-aminophenol type compounds and o- or p-phenylenediamine type compounds and salts thereof.

Preferably, p-phenylenediamine type compounds may be used, which are represented by the following formula [I].

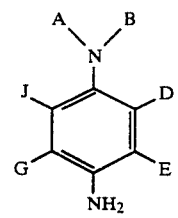

Formula [I]

In the formula, A and B represent a hydrogen atom or an alkyl group, or A and B may form a heterocyclic ring together with a nitrogen atom; D, E, G and J represent a hydrogen atom, a halogen atom, a hydroxy group, an amino group, an alkoxy group, an acylamide group, an arylsulfonamide group, an alkylsulfonamide group or an alkyl group. As the alkyl group represented by A and B, those having 1 to 6 carbon atoms, particularly 1 to 4 carbon atoms, are preferred. For example, a methyl group, an ethyl group and a butyl group may be included. These alkyl groups may also have substituents, and examples of the substituents in that case may include a hydroxyl group, an ureido group, a tetrahydrofuryl group, a carboxyl group, a methanesulfonamide group, a sulfo group, a methoxy group, an ethoxy group, a methoxyethoxy group, a methoxyethoxyethoxy group, a methoxytetraethoxy group, etc. Further preferably, a hydroxyl group and a methanesulfonamide group may be employed.

As D, G and J, a hydrogen atom, an alkoxy group and an alkylsulfonamide group, an arylsulfonamide group are preferred, more preferably a hydrogen atom. As E, a hydrogen atom, an alkyl group, an acylamide group are preferred, more preferably an alkyl group having 1 to 3 carbon atoms, particularly a methyl group. As the salts of the compounds represented by the formula [I], there may included salts of organic acids or inorganic acids such as p-toluenesulfonic acid, sulfonic acid, sulfinic acid, sulfate esters, sulfamic acid, thiosulfate S-esters, carboxylic acid, phosphate esters, amidophosphoric acid, phosphoric acid, sulfurous acid esters, organic boron compounds, hydrochloric acid, sulfuric acid, etc. Particularly, p-toluenesulfonic acid salt, hydrochloric acid salt and sulfuric acid salt are preferred.

In the following, representative specific examples of the aromatic primary amine compound according to the present invention are shown, but the present invention is not limited thereto at all.

Exemplary compounds:
(1-1) N,N-diethyl-3-methyl-4-aminoaniline;
(1-2) N,N-diethyl-4-aminoaniline;
(1-3) N-carbamidomethyl-N-methyl-4-aminoaniline;
(1-4) N-carbamidomethyl-N-tetrahydrofurfuryl-3-methyl-4-aminoaniline;
(1-5) N-ethyl-N-carboxymethyl-3-methyl-4-aminoaniline;
(1-6) N-carbamidomethyl-N-ethyl-3-methyl-4-aminoaniline;
(1-7) N-ethyl-N-tetrahydrofurfuryl-3-methyl-4-aminophenol;
(1-8) 3-acetylamino-4-aminodimethylaniline;
(1-9) N-ethyl-N-β-methanesulfonamidoethyl-4-aminoaniline;

(1-10) N-ethyl-N-β-methanesulfonamidoethyl-3-methyl-4-aminoaniline;
(1-11) N-methyl-N-β-sulfoethyl-p-phenylenediamine;
(1-12) N-ethyl-N-hydroxyethyl-3-methyl-4-aminoaniline;
(1-13) N-ethyl-N-{2-(2-methoxyethoxy)ethyl}-3-methyl-4-aminoaniline;
(1-14) N-ethyl-N-{2-[2-(2-methoxyethoxy)ethoxy]ethyl}-3-methyl-4-aminoaniline;
(1-15) N-ethyl-N-[2-{2-[2-(2-methoxyethoxyethoxy)ethoxy]ethoxy}ethyl]-3-methyl-4-aminoaniline;
(1-16) ethyl-3-methanesulfonamidoethyl-4-aminoaniline.

The salt of the compound represented by the formula [I] is generally water-soluble and can be readily dissolved water or in a buffer.

The active methylene compound or phenol compound which can be used in the present invention is a compound which is coupled with the oxidized product of an aromatic primary amine compound to form a dye and, for reducing solubility of said dye formed in water, it may be an active methylene compound substituted with an appropriate substituent or a phenol compound substituted on the benzene ring with an appropriate substituent. Among them, first concerning active methylene compound, it is well known as a yellow coupler or a magenta coupler in silver halide color photography. Also, there is included the case in which one of the two hydrogen atoms of the active methylene is substituted with the group which is eliminated through the coupling reaction with the oxidized product of an aromatic primary amine compound. These compounds are described in T. H. James, "The Theory of the Photographic Process" Third Edition, Chapter 17 and Fourth Edition, Chapter 12.

As the magenta coupler, there may be included 5-pyrazolone derivatives, pyrazolo[2,3-a]benzimidazole derivatives, pyrazolo-(3,2-c)-5-triazole derivatives, cyanoacetyl substituted heterocyclic compounds (cyanoacetyl, chromane, -thiophene, -quinoline derivatives), indazolone derivatives, as preferable examples.

As the yellow coupler, there may be included acylacetonitrile derivatives, acylacetamide derivatives, 1,3-diketone derivtives.

In the following, representative specific examples of the active methylene compound of the present invention are set forth, but the present invention is not limited thereto.

Exemplary compounds:

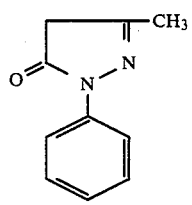

M - 1

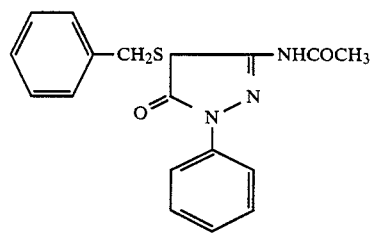

M - 2

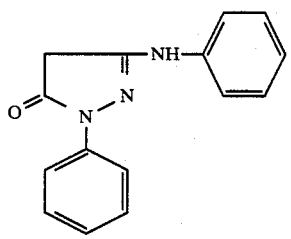

M - 3

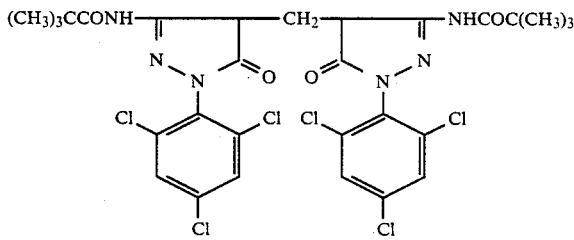

M - 4

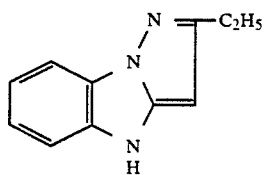 M-5
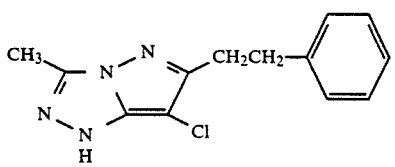 M-6
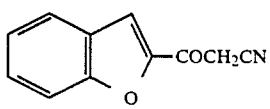 M-7
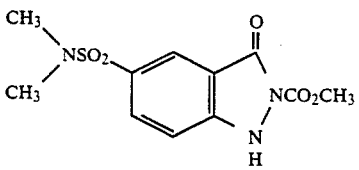 M-8
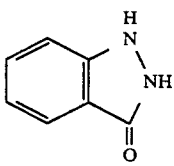 M-9
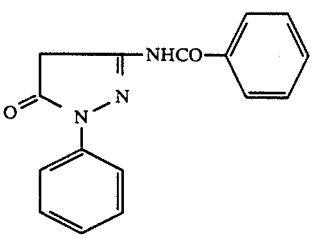 M-10
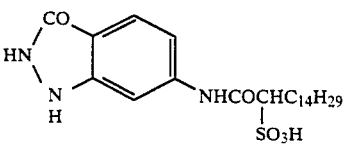 M-11
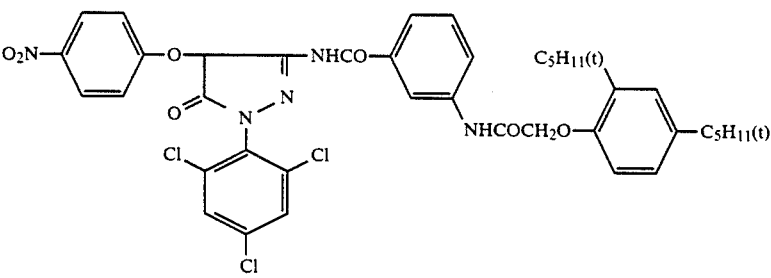 M-12

M - 13
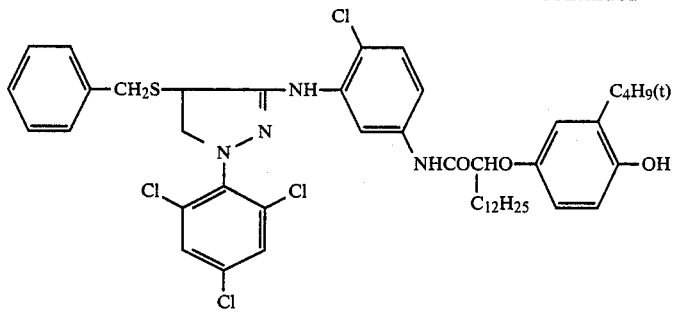
Y - 1
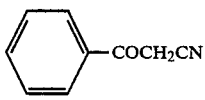
Y - 2
Y - 3
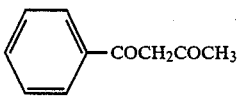
Y - 4
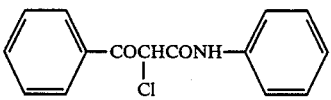
Y - 5
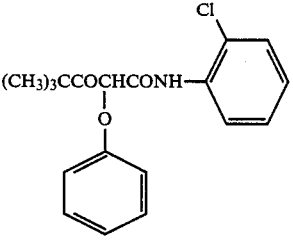
Y - 6
Y - 7
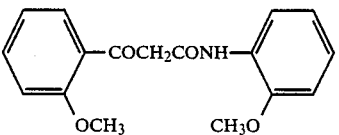
Y - 8
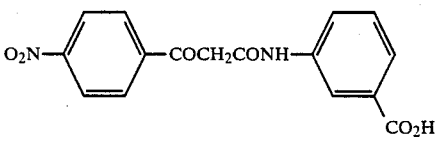
Y - 9
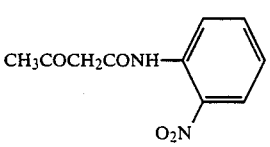

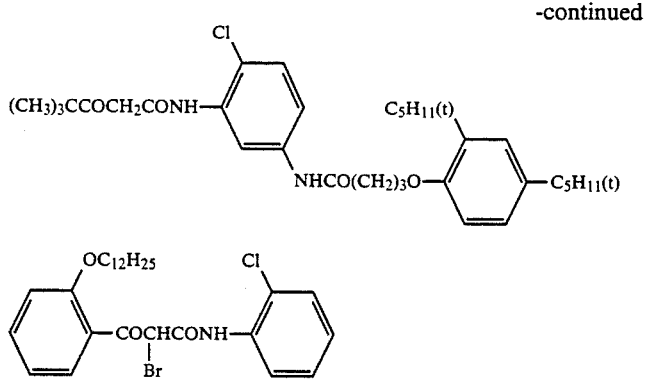

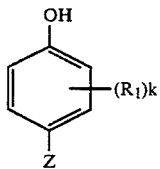

Next, preferable among phenol compounds are phenol compounds which are not substituted at the 4-position or substituted with a group (hereinafter called eliminable group) or an atom (hereinafter called eliminable atom) which can be eliminated during the coupling reaction with the oxidized product of an aromatic primary amine compound.

The phenol compounds advantgeously used in the present invention are represented by the following formula [II]: Formula [II]:

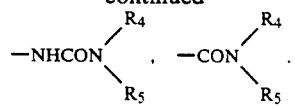

In the formula, $R_1$ represents a monovalent organic group or atom, Z represents a hydrogen atom, an eliminable group or an eliminable atom, and k represents an integer of 1 to 4.

The eliminable atom represented by Z may include halogen atoms, such as a chlorine atom, a bromine atom. Preferably, it is a chlorine atom.

The eliminable group represented by Z may include, for example, $-OR_2$, $-OCOR_2$, $-OSO_2R_2$, $-SR_2$, $-OCONHR_2$, $-SO_2NHR_2$,

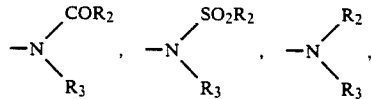

—SCN. Here, $R_2$ and $R_3$ represent a hydrogen atom, an aliphatic hydrocarbon residue, an alicyclic compound residue, an aryl group or a heterocyclic residue.

The atom represented by $R_1$ may include halogen atoms, such as a chlorine atom, a bromine atom. Preferably, it is a chlorine atom.

The monovalent organic group represented by $R_1$ may be, for example, an aliphatic hydrocarbon residue, an alicyclic compound residue, a heterocyclic residue, an aryl group, —SCN, $-OR_4$, $-OCOR_4$, $-OSO_2R_4$, $-SR_4$, $-OCONHR_4$, $-SO_2NHR_4$,

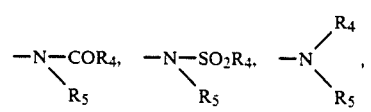

-continued $$-NHCON\begin{matrix}R_4\\ \\R_5\end{matrix}, \quad -CON\begin{matrix}R_4\\ \\R_5\end{matrix}.$$

Here, $R_4$ and $R_5$ represent a hydrogen atom, an aliphatic hydrocarbon residue, an alicyclic compound residue, an aryl group or a heterocyclic residue.

The aliphatic hydrocarbon residues represented by $R_1$, $R_2$, $R_3$, $R_4$ and $R_5$ may be either saturated or unsaturated, and also straight or branched. And, they are preferably alkyl groups (e.g. a methyl group, an ethyl group, a propyl group, an isopropyl group, a butyl group, a t-butyl group, an isobutyl group, a dodecyl group, an octadecyl group) or alkenyl groups (e.g. an allyl group, an octenyl group).

The alicyclic compound residues represented by $R_1$, $R_2$, $R_3$, $R_4$ and $R_5$ may include those which are 5- to 6-membered, for example, a cyclopentyl group and a cyclohexyl group.

The heterocyclic residue represented by $R_1$, $R_2$, $R_3$, $R_4$ and $R_5$ may include a pyridinyl group, a pyrazinyl group, a pyridazinyl group, a quinolyl group, a pyrrolidyl group, a furalyl group, a thienyl group, a piperidyl group, a pyrrolyl group, a pyrrolinyl group, a tetrazolyl group, a thiazonyl group, an imidazolyl group, a morpholyl group, a furyl group, an oxazolyl group, a thiazolyl group, a benzimidazolyl group, a benzoxazolyl group, a benzthiazolyl group, etc. as representative examples.

The aryl group represented by $R_1$, $R_2$, $R_3$, $R_4$ and $R_5$ may include a phenyl group or a naphthyl group, as representative examples.

As the nonaromatic ring fused to the benzene ring formed by bonding of the above two $R_1$, there may be included 5-to 6-membered rings such as cyclopentane ring, cyclohexane ring and cylohexene ring.

As the aromatic ring fused to the benzene ring formed by bonding of the above two $R_1$'s, particularly $R_1$ at the 5-and 6-positions, there may be included 5- to 6-membered rings such as a phenyl group, a pyridinyl group, a pyrazinyl group, a pyridazinyl group, a pyrrolidyl group, a furalyl group, a thienyl group, a piperidyl group, a pyrrolyl group, a pyrrolinyl group, a thiazinyl group, an imidazolyl group, a furyl group, an oxazolyl group, a thiazolyl group, etc. Preferably, it is a phenyl group.

The aliphatic hydrocarbon residue, the alicyclic compound residue, the aryl group, the heterocyclic residue and the nonaromatic ring or the aromatic ring formed by bonding of the above two R₁'s described above, which are represented by $R_1$, $R_2$, $R_3$, $R_4$ and $R_5$, may have also substituents.

Examples of such substituents may include halogen atoms (e.g. chlorine atoms, fluorine atoms), a nitro group, a cyano group, a hydroxy group, a keto group, a carboxyl group, a sulfo group, an amino group (e.g. amino, alkylamino, dialkylamino, anilino, N-alkylanilino), an alkyl group (e.g. methyl, propyl, isopropyl, t-butyl, octadecyl, cyanoalkyl, haloalkyl, aralkyl), an alkenyl group, an aryl group (e.g. phenyl, tolyl, acetylaminophenyl, 4-lauroylaminophenyl, ethoxyphenyl), a heterocyclic residue, an alkoxy group (e.g. ethoxy, phenoxy, methoxy, tetradecyloxy), an aryloxy group (e.g. phenoxy, 2,4-di-t-amylphenoxy, p-t-butyl-phenoxy, 4-n-dodecyloxyphenoxy, 4-hydroxy-3-t-butylphenoxy, 4-hydroxy-3-n-butylphenoxy), an arylthio group, an amide group (e.g. acetamide, methanesulfonamide, p-dodecylbenzenesulfonamide), a carbamoyl group (e.g. N-p-carboxymethoxyphenyl-carbamoyl, N,N-dihexylcarbamoyl, N-benzylcarbamoyl, N-ethylcarbamoyl, N-methoxyethylcarbamoyl), a sulfamoyl group (e.g. N,N-diethylsulfamoyl), an alkylsulfonyl group, an arylsulfonyl group (e.g. benzenesulfonyl, m-chlorobenzenesulfonyl), an acyl group (e.g. acetyl, p-chlorobenzoyl, benzoyl), an acyloxy group (e.g. acetyloxy, m-chlorobenzoyloxy), an acyloxycarbonyl group and an alkoxycarbonyl group (e.g. N-methoxyethylcarbamoylmethoxycarbonyl, ethoxycarbonyl, methoxycarbonyl, triethoxycarbonyl), an aryloxycarbonyl group (e.g. phenoxycarbonyl, p-nitrophenoxycarbonyl), an arylthiocarbonyl group (e.g. phenylthiocarbonyl), an imide group (e.g. succinimide, octadecyl succinimide).

Representative specific examples of the phenol compound of the present invention are shown below, but the compounds to be used in the present invention are not limited thereto.

Exemplary compounds:
(2-1) 2-benzyl-4-chlorophenol;
(2-2) N-benzoyl-4,6-dichloro-5-methyl-2-aminophenol;
(2-3) 2-benzoylamino-5-acetamino-4-chlorophenol;
(2-4) 4-chloro-1-naphthol;
(2-5) 4-methoxy-1-naphthol;
(2-6) 2,4-dichloro-1-naphthol;
(2-7) 1-hydroxy-4-bromo-N-ethyl-2-naphthoamide;
(2-8) 1-hydroxy-4-methoxy-N-propyl-2-naphthoamide;
(2-9) 2,6-dibromo-1,5-dihydroxy-naphthalene;
(2-10) 1-hydroxy-5-phenylsulfonamidenaphthalene;
(2-11) 1-hydroxy-2,4-dichloro-5-nitro-naphthalene;
(2-12) 4-bromo-1-naphthol;
(2-13) 4-ethoxy-1-naphthol;
(2-14) 4-(n-butoxy)-1-naphthol;
(2-15) 4-sulfo-1-naphthol;
(2-16) 4-(2-methoxyethoxy)-1-naphthol;
(2-17) 4-methylthio-1-naphthol;
(2-18) 4-phenylthio-1-naphthol;
(2-19) 4-phenylazo-1-naphthol;
(2-20) 4,5-dimethoxy-1-naphthol;
(2-21) 4-ethanesulfonamide-1-naphthol;
(2-22) 4-(2-aminophenylazo)-2-propyl-1-naphthol;
(2-23) 4,7-dimethoxy-2-methoxymethyl-1-naphthol;
(2-24) 4-chloro-2-dimethylcarbamoyl-1-naphthol;
(2-25) 4-(1-carboxybutoxy)-1-naphthol;
(2-26) 4-chloro-2-acetylamino-1-naphthol.

For forming and depositing a dye on the complex conjugate of a specific component and a peroxidase labelled body carried on a support, the support may be dipped in the substrate test solution for color formation. The substrate test solution for color formation is prepared by dissolving the three of hydrogen peroxide, an aromatic primary amine compound, an active methylene or a phenol compound in a buffer with an appropriate pH. The active methylene or phenol compound may be added as a solution dissolved in a small amount of a hydrophilic organic solvent such as methanol, ethanol, DMF, etc. The molar ratio of the aromatic primary amine compound to the active methylene or phenol compound may be suitably from 1:100 to 100:1, particularly preferably from 1:10 to 10:1.

After the dye is sufficiently formed and deposited on the support through the enzyme reaction, unreacted substances are washed away to stop the reaction.

The information about the dye formed can be read by observation with eyes, or according to a technologically known method, for example, by use of a spectrophotometer.

DESCRIPTION OF EXAMPLES

The present invention is described below in more detail by referring to Examples, but the scope of the present invention is not limited at all by these Examples.

EXAMPLE 1

Measurement of antigen on nitrocellulose film

A nitrocellulose film (produced by Biorad Co; thickness 0.45 μm) was washed with pure water, then dried on air and on the film was spotted 1 μl of a goat IgG subjected to step dilution with a phosphate buffer (hereinafter called PBS).

After drying on air, blocking was effected overnight at 4° C. with a 1% bovine serum albumin (BSA)-PBS solution, and subsequently the reaction was conducted at 4° C. for 2 hours with a peroxidase labelled rabbit anti-goat IgG antibody (produced by Cappel Co.; diluted to 1500-fold with 1% BSA-PBS solution). After washing 5 times with a 0.05% Tween-20 (polyoxyethylene sorbitane monolaurate; produced by Wako Junyaku K.K.)-PBS solution, the product was dipped in a substrate test solution for color formation. The following 5 kinds were employed as the substrate test solution for color formation, and the respective color formed states were compared with each other. (1) The test solution was prepared by dissolving 3 mg of 4-chloro-1-naphthol in 1 ml of methanol, adding 5 ml of 0.05 M Tris HCl buffer (pH 7.4, containing 200 mM NaCl; hereinafter called TBS) and further adding 20 μl of 3% hydrogen peroxide.

(2) The test solution was prepared by dissolving 3 mg of the exemplary compound M-1 in 1 ml of methanol, adding 5 ml of TBS, adding 1 mg of N-ethyl-N-β-methanesulfonamidoethyl-3-methyl-4-aminoaniline 3/2 sulfate monohydrate, and further adding 20 μl of 3% hydrogen peroxide.

(3) The test solution was prepared by adding N,N-diethyl3-methyl-4-aminoaniline hydrochloride in place of N-ethyl-N-β-methanesulfonamidoethyl-3-methyl-4-aminoaniline 3/2 sulfate monohydrate in the test solution of (2).

(4) The test solution was prepared by adding 1 mg of N-ethyl-N-β-methanesulfonamidoethyl-3-methyl-4-aminoaniline 3/2 sulfate monohydrate to the test solution of (1).

(5) The test solution was prepared by adding 1 mg of N,N-diethyl-3-methyl-4-aminoaniline hydrochloride to the test solution of (1).

After reaction for 15 minutes, the product was thoroughly washed with water and dried on air. When the substrate test solution for color formation (1) was employed, the spot was grayish violet and only 10 ng of the goat IgG could be detected, but when the substrate test solutions for color formation (2), (3), (4) and (5) of the present invention were employed, the spot of 1 ng of the goat IgG could be detected.

EXAMPLE 2

Measurement of glycolipid antigen on TLC plate

On a TLC plate (Polygram, produced by Machery-Nagel Co.) were spotted solutions comprising $GM_1$ ganglioside purified by separation from bovine brain with various dissolved amounts in a mixture of chloroform and methanol, and development was effected with a developing solution of chloroform:methanol:0.5% aqueous calcium chloride solution (volume ratio: 55:45:10). After drying on air, blocking was conducted with 1% ovalbumin-PBS solution at 4° C. overnight, and the reaction was carried out with an anti-$GM_1$ ganglioside antiserum prepared in rabbit (diluted to 500-fold with 1% polyvinylpyrrolidone, 1% ovalbumin-PBS solution) at 37° C. for 2 hours.

After washing 3 times with a 0.05% Tween-20-PBS solution, the reaction was carried out with a peroxidase labelled goat anti-mouse immunogloblin antibody (produced by Cappel Co.; diluted to 1500-fold with 3% polyvinylpyrrolidone-PBS solution) at 37° C. for 2 hours.

After washing 3 times with a 0.05% Tween-20-PBS solution, the product was dipped in a substrate test solution for color formation. The following 5 kinds of substrate test solutions for color formation were employed, and the color formed states in the respective cases were compared with each other.

(1) The test solution was prepared similarly as in the case of the test solution of (1) in Example 1.

(2) The test solution was prepared by dissolving 3 mg of the exemplary compound M-2 in 1 ml of methanol, adding 5 ml of TBS, adding 1 mg of N-ethyl-N-hydroxyethyl-3-methyl-4-aminoaniline sulfate monohydrate, and further adding 20 μl of 3% hydrogen peroxide.

(3) The test solution was prepared by use of the exemplary compound Y-2 in place of the exemplary compound M-1 in the test solution of (2).

(4) The test solution was prepared by adding 1 mg of N-ethyl-N-hydroxylethyl-3-methyl-4-aminoaniline sulfate monohydrate to (1).

(5) The test solution was prepared by use of 4-methoxyl-naphthol in place of 4-chloro-1-naphthol in the test solution of (4).

After reaction for 15 minutes, the product was thoroughly washed with water and dried on air.

When the substrate test solution for color formation of (1) was employed, the spot was grayish violet and only 4 ng of $GM_1$ ganglioside could be detected, but when the test solutions of (2), (3), (4) and (5) of the present invention were employed, the spot was sharp and detection was possible to 0.2 ng.

EXAMPLE 3

Screening of antibody and hybridoma

An amount of 50 μg of $\alpha_1$-antitrypsin was injected together with Freund's complete adjuvant intraperitoneally into Balb/C mouse (female, 6 weeks old). After 3 weeks, further 50 μg of $\alpha_1$-antitrypsin was injected together with Freund's incomplete adjuvant intraperitoneally, followed further after 2 weeks by intravenous injection of a solution comprising 30 μg of $\alpha_1$-antitrypsin dissolved in PBS. Three days after the final immunization, spleen cells were taken out and fused in a conventional manner with mouse myeloma cells x 63.6.5.3. The fused cells were distributed on 5 sheets of 96-well plates and cultured in HAT selective medium. After 3 weeks after fusion, for the wells in which colonies of the hybridoma were formed, the antibody was assayed according to the following method.

A nitrocellulose was cut into 4 mm squares and each sheet was spotted with 1 μl of a PBS solution with 500 μg/ml of $\alpha_1$-antitrypsin. Each one sheet was added per one well of the 96-well microtiter plate, and blocking was performed with 1% BSA-PBS solution at 4° C. overnight. After washing with PBS, 40 μl of the culture supernatant of the hybridoma was added and reaction was carried out at room temperature for 2 hours. After washing 3 times with 0.05% Tween-20-PBS solution, 40 μl of a peroxidase labelled goat anti-mouse immunoglobulin antibody (produced by Cappel Co.; diluted to 1500-fold with 1% BSA-PBS solution), and reaction was carried out at room temperature for 2 hours. After washing 3 times with 0.05% Tween-20-PBS solution, 150 μl of a substrate test solution for color formation was added, and the sample in which a dye was formed on the nitrocellulose was evaluated as positive for antibody activity. The following 3 kinds of substrate test solutions for color formation were prepared.

(1) The test solution was prepared similarly as in the case of (1) in Example 1.

(2) The test solution was prepared by dissolving 3 mg of the exemplary compound Y-2 in 1 ml of methanol, adding 5 ml of TBS, adding 1 mg of N,N-diethyl-4-aminoaniline sulfate and further adding 20 μl of 3% hydrogen peroxide.

(3) The test solution was prepared by adding 1 mg of N,N-diethyl-4-aminoaniline sulfate to the test solution of (1).

Of the 350 wells measured, in the case of the test solution (1), antibody activity positive hybridomas could be detected in only 15 wells, but antibody activity positive hybridomas could be detected in 23 wells when the test solutions (2) and (3) of the present invention were employed.

We claim:

1. A method for measuring a specific component, said method comprising the steps of
    forming and providing a complex conjugate comprising a specific component to be measured and a peroxidase labelled ligand carried on a support; and
    forming and depositing a water-insoluble dye on said complex conjugate through the enzyme reaction or peroxidase with hydrogen peroxide, a p-phenylenediamine type aromatic primary amine compound and either one of an active methylene compound or a phenol compound, wherein said aromatic primary amine compound is represented by the formula:

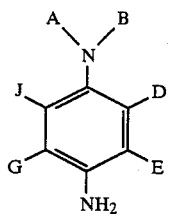

Formula [I]

wherein A and B each represents a hydrogen atom, an alkyl group, or A and B may form a heterocyclic ring together with a nitrogen atom; D, E, G and J each represents a substituent selected from the group consisting of a hydrogen atom, a halogen atom, a hydroxy group, an amino group, an alkoxy group, an acylamide group, an aryl-sulfonamide group, an alkylsulfonamide group and an alkyl group, or a salt of said compound.

2. A method for measuring a specific component according to claim 1, wherein said specific component is directly or indirectly carried on the support before the reaction with said labelled ligand to form a complex conjugate.

3. A method for measuring a specific component according to claim 1, wherein said complex conjugate is formed before said complex conjugate is directly or indirectly carried on the support.

4. A method for measuring a specific component according to claim 1, wherein said active methylene compound is selected from the group consisting of an acylacetonitrile derivative, an acylacetamide derivative, a 1,3-diketone derivative, a 5-pyrazolone derivative, a pyrazolol(2,3-a)benzimidazole derivative, a pyrazolo-(3,2-c)-5-triazole derivative, a cyanoacetyl substituted heterocyclic compound and an indazolone derivative.

5. A method for measuring a specific component according to claim 1, wherein said phenol compound is represented by the formula:

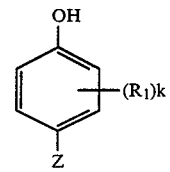

wherein $R_1$ represents a monovalent organic group or atom, Z represents a hydrogen atom or a group or atom eliminable during the coupling reaction with the oxidized product of said aromatic primary amine compound, and k represents an integer of 1 to 4.

6. A method for measuring a specific component according to claim 5, wherein said phenol compound has a phenyl ring bonded between $R_1$ substituents at the 5- and 6- positions.

* * * * *

UNITED STATES PATENT AND TRADEMARK OFFICE
CERTIFICATE OF CORRECTION

PATENT NO. : 4,921,791

DATED : May 01, 1990

INVENTOR(S) : Masahiko Yamasaki et al.

It is certified that error appears in the above-identified patent and that said Letters Patent is hereby corrected as shown below:

Claim 1, Column 16, Line 62, "or" should be --of--.

Signed and Sealed this

Twentieth Day of October, 1992

*Attest:*

DOUGLAS B. COMER

*Attesting Officer*       *Acting Commissioner of Patents and Trademarks*